United States Patent [19]

Wideman et al.

[11] 4,382,152

[45] May 3, 1983

[54] PROCESS FOR THE CONVERSION OF TERPENES TO CYMENES

[75] Inventors: Lawson G. Wideman, Tallmadge; Joseph A. Kuczkowski, Munroe Falls, both of Ohio

[73] Assignee: The Goodyear Tire & Rubber Company, Akron, Ohio

[21] Appl. No.: 311,220

[22] Filed: Oct. 14, 1981

[51] Int. Cl.³ .................. C07C 5/36; C07C 15/02
[52] U.S. Cl. .............................. 585/430; 585/432
[58] Field of Search ............................ 585/430, 432

[56] References Cited

U.S. PATENT DOCUMENTS

| | | | |
|---|---|---|---|
| 1,746,532 | 2/1930 | Humphrey | 585/432 |
| 2,052,917 | 9/1936 | Bergström et al. | 585/432 |
| 2,211,432 | 8/1940 | Palmer et al. | 585/432 |
| 2,376,252 | 5/1945 | Hull | 585/432 |
| 2,376,309 | 5/1945 | Dixon | 585/430 X |
| 2,376,310 | 5/1945 | Dixon | 585/430 X |
| 2,420,749 | 5/1947 | Ipatieff et al. | 585/432 |
| 2,745,887 | 5/1956 | Pines et al. | 585/432 |
| 2,754,338 | 7/1956 | Pines | 585/432 |
| 2,754,339 | 7/1956 | Pines | 585/432 X |

*Primary Examiner*—Paul F. Shaver
*Attorney, Agent, or Firm*—D. O. Nickey

[57] ABSTRACT

There is disclosed a process for the conversion of terpenes to cymenes which comprises contacting at least one terpene, selected from the group comprised of mono- and bi-cyclic unsaturated hydrocarbons having the formula $C_{10}H_{16}$; with an alkali metal carbonate catalyst on a support at a temperature of 300° to 475° C.

30 Claims, No Drawings

PROCESS FOR THE CONVERSION OF TERPENES TO CYMENES

TECHNICAL FIELD

This invention is concerned with the economic conversion of terpenes to cymenes. More specifically, this invention is concerned with a process to convert a renewable hydrocarbon source, that being the volatile oil present in trees, to a compound that can provide an alternative source of hydrocarbon feed stocks that are nonpetroleum based. The process of the present invention accomplishes the conversion of terpenes to cymenes by contacting at least one terpene, which is a mono- or bi-cyclic unsaturated hydrocarbon having the formula $C_{10}H_{16}$; with an alkali metal carbonate catalyst on a support at a temperature of 300° to 475° C.

BACKGROUND ART

Turpentine is the general term for the volatile oil present in trees, primarily coniferous trees. Chemically, it is predominately a mixture of unsaturated mono- and bi-cyclic $C_{10}H_{16}$ hydrocarbons. The principal component is alpha-pinene, which is present in the turpentine from all species of turpentine bearing trees.

The composition of the turpentine is determined by the species of the tree. A chromatograph of the turpentine makes a good fingerprint for identifying the species.

Although over thirty compounds have been identified in turpentine only a few have commercial significance, that is, they can be separated in high purity for subsequent use. Alpha-pinene, beta-pinene, and beta-phellandrene and dipentene are present in large enough volume in gum or sulfate turpentines of most species to make isolation feasible. $\Delta$-3 carene is present in large quantities in certain species, especially in the northwestern and Scandinavian pines. The terpenes as one would expect will undergo numerous reactions including hydrogenation, isomerization, polymerization, oxidation, halogenation, esterification and dehydrogenation.

There has been and continues to this day investigations concerning the production of high volume chemicals from nonpetroleum base sources. Trees, especially, coniferous trees, are a renewable resource that can be ground into wood chips and have extracted therefrom resins and terpenes. Terpenes are therefore a renewable resource that may be used to replace the present petroleum base source of most of industry's hydrocarbons. However, a turpentine or a mixture of terpenes, in and of themselves, are not a commercially significant hydrocarbon feed stock. Therefore, a process that will readily convert a terpene or a turpentine feed stock into a valuable or commercially more acceptable compound is highly desirable.

In the past numerous publications have reported the conversion of turpentine to various chemical compounds using numerous reaction conditions and catalysts. More specifically, Mizrahi and Nigam, (J. Chromatog., 25 (1966) pp. 230–241) report the dehydrogenation of seven mono-terpenes to para-cymene using catalytic dehydrogenation in a reaction gas chromatograph on a micro scale. Mizrahi and Nigam disclose the use of platinum on alumina to obtain p-cymene from hydrocarbons.

The prior art also discloses the vapor phase dehydrogenation of pinene to p-cymene through the use of platinized charcoal. (J. Chem. Soc. (1940) pp 1139 to 1147). However, none of the prior art publications disclose or suggest the process for the conversion of terpenes to cymenes which comprises contacting at least one terpene selected from the group comprised of mono- and bi-cyclic unsaturated hydrocarbons having the formula $C_{10}H_{16}$; with an alkali metal carbonate catalyst on a support at a temperature of 300° to 475° C. at a LHSV of 0.20 to 20.

DISCLOSURE OF THE INVENTION

There is disclosed a process for the conversion of terpenes to cymenes which comprises contacting at least one terpene, selected from the group comprised of mono- and bi-cyclic unsaturated hydrocarbons having the formula $C_{10}H_{16}$; with an alkali metal carbonate catalyst on a support at a temperature of 300° to 475° C.

Terpenes in the strict sense are volatile hydrocarbons of the empirical formula $C_{10}H_{16}$. In a wider sense the term includes sesquiterpenes, $C_{15}H_{24}$, diterpenes, $C_{20}H_{32}$, and higher polymers. In a still looser sense, the term includes various oxygen containing compounds derived from terpene hydrocarbons, such as alcohols, ketones and camphors. The terpenes are based on the isoprene unit, $C_5H_8$, and may be either acyclic or cyclic with one or more benzenoid groups. Representative of the terpenes that can be used in the process of the present invention are alpha-pinene, beta-pinene, limonene, $\Delta$-3 carene, and terpinolene.

The conversion of terpenes to cymenes is of significant importance since it could provide a renewable hydrocarbon source for compounds such as cresols, dimethylstyrenes, and phthalic acids.

Representative of the alkali metal carbonae catalysts that are useful in the process of this invention are sodium carbonate, lithium carbonate and potassium carbonate or mixtures thereof. Preferably, sodium or potassium carbonates are used since they are less costly and tend less toward side reactions. The process of the present invention is conducted using the alkali metal carbonate supported on a carrier. Supporting the alkali metal carbonate on a carrier is required since this provides good surface area of catalyst per gram of material. Representative of the carriers upon which the alkali metal carbonates can be supported are silica; aluminum oxide ($Al_2O_3$); magnesium oxide (MgO); carbon (C) and titanium dioxide ($TiO_2$), however, any support that does not detrimentally effect the activity of the alkali metal carbonate and has a surface area of at least 10 $m^2/gm$ may be used.

Aluminum oxide ($Al_2O_3$) and magnesium oxide (MgO) are the preferred supports for the alkali metal carbonate. For production of the support a great variety of modifications of aluminum oxide are suitable, such as $\alpha$-, $\kappa$-, H-, $\gamma$-, $\eta$- or $\sigma$-modifications; however, $\gamma$ aluminum oxide is generally preferred since it is easiest in its manipulation and yields satisfactory results.

To ensure a good efficiency of the catalyst the specific surface area of the support material should generally be larger than 20 $m^2/gm$, preferably larger than 100 $m^2/gm$.

The catalyst system should contain from 2–25 percent by weight of the alkali metal carbonate (based on the finished catalyst). At concentrations below 5 percent by weight a lower yield of cymenes is realized and at concentrations above 25 percent by weight, the catalyst is more difficult to handle since it is less pourable and no advantage in yield is realized.

Preferably, however, the catalyst contains about 5 to 15 percent by weight of alkali metal carbonate, since high activity combined with excellent pourability is found in this range. Excellent results are obtained with the catalyst containing about 10 percent by weight of alkali metal carbonate.

The amount of catalyst employed is related to the LHSV of the reaction system. The LHSV should be large enough, above 0.20 so as to effect efficient conversion of terpenes to cymenes. A LHSV of 0.4 to 10 is particularly advantageous. Within this ratio the reaction can be controlled to give high yields of cymene.

The manufacturing methods for catalysts containing alkali metals on aluminum oxide supports have been wellknown to those skilled in the art for years and are disclosed in numerous popular publications and also in numerous patents, such as U.S. Pat. No. 2,836,633.

In a preferred embodiment the catalyst is produced in accordance with a very simple method by first predrying the support material for about 5 hours at a temperature of about 200°–400° C. After drying, the support material is allowed to cool to about 100° C. and then the corresponding amount of alkali metal carbonate is added in a mechanical mixing device under a protective gas atmosphere. At the temperature employed the metal carbonate uniformly distributes itself on a support material. In addition, the alkali metal carbonate may be dispersed upon carrier as an aqueous solution. If desired, the catalyst can further be subjected to high temperatures after treatment, by heating the same for about 2 to 20 hours at 200°–600° C.

After its manufacture the catalyst may be in the form of powder, granules, pellets or extrudates.

The temperature which the process of the present invention can be conducted ranges from 300° to 475° C. A more preferred temperature range is from 350° to 450° C. with the most preferred being 380° to 425° C.

The process of the present invention is conducted in a continuous manner, however, the concept may be altered to encompass a batch process. However, numerous operating difficulties and poor yields will result from the operation of the present invention in a batch or a semi-continuous nature. The process of the present invention is carried out in the vapor phase since the reaction temperature is greater than that of the boiling point of the starting materials.

A liquid hourly space velocity ratio or throughput of material through the reactor that is suitable for the process of the present invention is 0.20 to 20. Liquid hour space velocity, hereinafter known as LHSV, is meant to mean a volume of liquid throughput per gross volume of catalyst. A gross volume of catalyst is the actual volume plus the interstitial volume. For example, 90 ml of liquid feed stock is passed over 45 cc (gross volume) of catalyst in one hour to yield an LHSV of 2. See *Chem. Eng. Kinetics*, J. M. Smith, McGraw-Hill, N.Y., pp 99–100 (1956).

BEST MODE FOR CARRYING OUT THE INVENTION

The process of the present invention is generally carried out in a tubular reactor in an upflow or downflow manner. A preheater is used to vaporize the terpenes prior to passage through the reactor. The reaction can be carried out at atmospheric pressure or at superatmospheric pressure, there being no appreciable economic advantage to either. Proper temperature control of the catalyst bed and reaction wall temperatures is required to achieve satisfactory results. A flow of an inert gas, for example, nitrogen or carbon dioxide, is used as the carrier gas in the reactor. The reactor catalyst bed and the preheater are all brought up to the reaction temperature prior to introduction of the terpene stream. The terpene feed stream is volatized in the preheater and then is carried by the inert gas to the reactor which contains the catalyst bed. This rate of flow of material over the catalyst bed may range from 0.20 to 20 with a rate of 0.4 to 20 being more preferred and a rate of 0.4 to 10 being the most preferred.

The advantages obtainable by means of the present invention reside in that the aforementioned terpenes can be converted practically quantitatively into cymenes with a relatively inexpensive catalyst and within short reaction periods. The reaction product, cymenes, may be so pure that they can be utilized without further processing or purification to produce dimethylstyrenes.

PREPARATION OF THE CATALYST

A commercially available aluminum oxide having a surface area of 80–234 $m^2/gm$ and consisting of 98 percent by weight of $Al_2O_3$ wherein 95 percent is in the gamma form and 5 percent is in the alpha form is dried for 15 hours at 400° C. under nitrogen in a container equipped with an agitator. The aluminum oxide is then allowed to cool to 150° C. and a stoichiometric amount of the alkali metal carbonate is added thereto. The alkali metal carbonate in this case, specifically, sodium carbonate is distributed on the support by 10 hours of agitation. During the agitating step the temperature is gradually elevated to 400° C. After cooling the catalyst is ready for use.

EXAMPLE 1

Conversion of Turpentine to p-cymene with 10% $K_2CO_3/Al_2O_3$

A 10 inch by three-quarter inch stainless steel reactor was charged with 45 cc of 10 percent $K_2CO_3/Al_2O_3$ as the catalyst and flushed with a constant flow of 7 ml per minute of nitrogen. The turpentine feed analysis indicated that 54 percent was α-pinene, 34 percent β-pinene, 7 percent limonene, 1–2 percent p-menthane isomers (cis and trans), 1–2 percent terpinolene, 1–2 percent terpinene, 1–2 percent menthadienes and 1–2 percent Δ-3 carene. Turpentine was metered into the tubular reactor in a downflow manner. The turpentine contained 10 percent heptane as an internal gas chromatograph standard. A glass bead preheater was used to vaporize the feed prior to contact with the catalyst. Nitrogen as a carrier gas at 7 ml/min. was metered into the reactor concurrently with the turpentine stream. The reactor contained a heating jacket with manual temperature controls and a catalyst bed thermocouple array to monitor the internal temperature. The reactions were carried out at atmospheric pressure.

The tubular reactor and preheater were heated to the desired reaction temperature before introduction of the feed. The effluent stream from the reactor was condensed in a dry ice acetone bath prior to gas chromatograph and NMR analysis. The sensitivity of turpentine and p-cymene to the GC detector had been predetermined. The samples were collected after one hour on stream. The percent turpentine conversion and percent cymene selectivity for two runs is presented in Table 1 wherein conversion times selectivity equals yield.

TABLE (I)

| | | Turpentine to cymenes | | | |
|---|---|---|---|---|---|
| Catalyst | Surface Area | Reaction Temp (°C.) | Turpentine* Conversion (%) | cymenes* Selectivity (%) | LHSV |
| 10% $K_2CO_3$/$Al_2O_3$ | 234 $m^2$/gm | 400 | 100 | 72 | 0.24 |
| 10% $K_2CO_3$/$Al_2O_3$ | 234 $m^2$/gm | 450 | 100 | 70 | 0.24 |

*It is to be realized that % Conversion and % Selectivity can be used to calculate yield of products by weight, volume or on a molar basis.

EXAMPLE 2

Conversion of Limonene to p-cymene With 10 percent $K_2CO_3$ on Alumina

The reactor and reaction conditions were as described in Example 1. Table II presents the data collected for three runs.

TABLE II

| Catalyst | Surface Area | Reaction Temp (°C.) | Limonene Conversion % | p-Cymene Selectivity (%) | LHSV |
|---|---|---|---|---|---|
| 10% $K_2CO_3$/$Al_2O_3$ | 234 $m^2$/gm | 400° | 100 | 95 | 0.48 |
| 10% $K_2CO_3$/$Al_2O_3$ | 234 $m^2$/gm | 450° | 100 | 95 | 0.48 |
| 10% $K_2CO_3$/$Al_2O_3$ | 234 $m^2$/gm | 400° | 100 | 95 | 1.00 |

EXAMPLE 3

Conversion of Turpentine to Cymenes Over Alumina (Comparative Example)

The reactor and reaction conditions and turpentine feed stream and LHSV were as set out in Example 1 except that unloaded $Al_2O_3$ with a surface area of 234 $m^2$/gm was used as the catalyst. At 400° C., 100% conversion of turpentine with a selectivity of 38% to cymenes was realized. At 450° C., 100% conversion of turpentine with a selectivity of 31% cymenes was realized. Thus, it is evident that loading an alkali metal carbonate upon a support is necessary to achieve effective and economical conversion of turpentine to cymene.

EXAMPLE 4

Limonene to p-cymene with 10 percent $Na_2CO_3$/$Al_2O_3$

The reactor and reaction conditions were as set out in Example 1 except that a limonene feed stock was utilized and 10% $Na_2CO_3$ on $Al_2O_3$ was used as the catalyst. The surface area of the 10% $Na_2CO_3$ on alumina was varied as was the temperature and LHSV of the reaction. The results of the experiment are set out in Table III.

TABLE III

| The Conversion of Limonene to p-Cymene with 10% $Na_2CO_3$/$Al_2O_3$ | | | | | |
|---|---|---|---|---|---|
| Catalyst | Surface Area | Reaction Temp (°C.) | Limonene Conversion (%) | p-Cymene Selectivity (%) | LHSV |
| 10% $Na_2CO_3$/$Al_2O_3$ | (80 $m^2$/g) | 300 | 0 | 0 | 0.48 |
| " | " | 350 | 100 | 89 | 0.48 |
| " | " | 350 | 100 | 90 | 0.24 |
| " | " | 400 | 100 | 46 | 0.48 |
| " | " | 450 | 90 | 88 | 1.00 |
| " | (234 $m^2$/g) | 350 | 22 | 66 | 0.48 |
| " | " | 400 | 66 | 95 | 0.48 |
| " | " | 450 | 100 | 93 | 0.48 |

EXAMPLE 5

Δ-3 Carene to cymene

The reactor and reaction conditions were as set out in Example 1 except that Δ-3 carene was the feed stock. $Na_2CO_3$ and $K_2CO_3$ on alumina were used as the catalyst. The LHSV and temperatures were varied and the data is found in Table IV for six runs.

TABLE IV

| Catalyst | Surface Area | Reaction Temp. (°C.) | Δ-3 Carene Conversion (%) | Cymene Selectivity (%) | LHSV |
|---|---|---|---|---|---|
| $Na_2CO_3$/$Al_2O_3$ | 80–100 $m^2$/gm | 400 | 100 | 87 | 0.96 |
| $Na_2CO_3$/$Al_2O_3$ | " | 450 | 100 | 89 | 0.96 |
| $Na_2CO_3$/$Al_2O_3$ | " | 450 | 100 | 95 | 0.48 |
| $Na_2CO$/$Al_2O_3$ | " | 450 | 100 | 88 | 6.24 |
| $K_2CO_3$/$Al_2O_3$ | " | 400 | 100 | 93 | 0.24 |
| $K_2CO_3$/$Al_2O_3$ | " | 450 | 100 | 90 | 0.48 |

EXAMPLE 6

Limonene to p-cymene

The reactor and reaction conditions were as set out in Example 1 except that limonene was the feed stock and the inert support was changed from $Al_2O_3$ to $TiO_2$ and MgO. The results are contained in Table V.

EXAMPLE 7

Δ-3 Carene to cymene

The reactor and reaction conditions were as set out in Example 1 except that Δ-3 carene in the feed stock, the catalyst is $Na_2CO_3$ and the inert supports were $TiO_2$ and MgO. The results are set out in Table VI.

TABLE V

| Catalyst | Surface Area | Reaction Temp (°C.) | Limonene Conversion (%) | p-Cymene Selectivity (%) | LHSV |
|---|---|---|---|---|---|
| 10% $Na_2CO_3$ on $Al_2O_3$ | 234 $m^2$/gm | 400 | 66 | 95 | 0.48 |
| 10% $Na_2CO_3$ on $TiO_2$ | 60 $m^2$/gm | 400 | 80 | 76 | 0.48 |
| 10% $Na_2CO_3$ on MgO | 21 $m^2$/gm | 400 | 100 | 95 | 0.48 |

TABLE VI

| Catalyst | Surface Area | Reaction Temp (°C.) | Δ-3 carene Conversion (%) | Cymene Selectivity (%) | LHSV |
|---|---|---|---|---|---|
| 10% $Na_2CO_3$ on $TiO_2$ | 60 $m^2$/gm | 400 | 81 | 75 | 0.48 |
| 10% $Na_2CO_3$ on MgO | 21 $m^2$/gm | 400 | 100 | 95 | 0.48 |

INDUSTRIAL APPLICABILITY

The process of the present invention provides a means for the conversion of a renewable feed stock, that being turpentine, to aromatic compounds that are significantly more important as a commercial feed stock. In addition, the process of the present invention accomplishes this conversion without the use of expensive and sometimes easily poisoned catalysts, such as platinum on carbon, and does so in a highly efficient and very selective manner. Thus, the process of the present invention provides a viable and economic means for the conversion of a renewable hydrocarbon feed stock into a more commercially acceptable aromatic feed stock.

While certain representative embodiments and details have been shown for the purpose of illustrating the invention, it will be apparent to those skilled in this art that various changes and modifications may be made therein without departing from the scope of the invention.

We claim:

1. A process for the conversion of terpenes to cymenes which comprises contacting at least one terpene selected from the group comprised of mono- and bicyclic unsaturated hydrocarbons having the formula $C_{10}H_{16}$, with an alkali metal carbonate catalyst on a support at a temperature of 300° to 475° C.

2. A process according to claim 1 wherein the terpenes are selected from the group consisting of α-pinene, β-pinene, limonene, p-menthane, (cis and trans isomers) terpinolene, terpinene, menthadiene and Δ-3 carene.

3. A process according to claim 1 wherein the alkali metal carbonate is selected from the group consisting of $Na_2CO_3$, $Li_2CO_3$ and $K_2CO_3$.

4. A process according to claim 1 wherein the alkali metal carbonate catalyst is supported on a carrier selected from the group consisting of silica, aluminum oxide, magnesium oxide, carbon and titanium dioxide.

5. A process according to claim 1 wherein the temperature of the reaction is from 350° to 450° C.

6. A process according to claim 1 wherein the temperature is from 380° to 425° C.

7. A process according to claim 1 wherein the alkali metal carbonate is sodium carbonate and the support is titanium dioxide.

8. A process according to claim 1 wherein the alkali metal carbonate is $K_2CO_3$ and the support is magnesium oxide.

9. A process for the conversion of terpenes to cymenes which comprises contacting at least one terpene selected from the group comprised of mono- and bicyclic unsaturated hydrocarbons having the formula $C_{10}H_{16}$, with an alkali metal carbonate catalyst on a support that has a surface area of at least 10 $m^2$/gm, at a temperature of 300° to 475° C.

10. A process according to claim 9 wherein the terpenes are selected from the group consisting of α-pinene, β-pinene, limonene, p-menthane, (cis and trans isomers) terpinolene, terpinene, menthadiene and Δ-3 carene.

11. A process according to claim 9 wherein the alkali metal carbonate is selected from the group consisting of $Na_2CO_3$, $Li_2CO_3$ and $K_2CO_3$.

12. A process according to claim 9 wherein the alkali metal carbonate catalyst is supported on a carrier selected from the group consisting of silica, aluminum oxide, magnesium oxide, carbon and titanium dioxide.

13. A process according to claim 9 wherein the temperature of the reaction is from 350° to 450° C.

14. A process according to claim 9 wherein the temperature is from 380° to 425° C.

15. A process according to claim 9 wherein the alkali metal carbonate is sodium carbonate and the support is titanium dioxide.

16. A process according to claim 9 wherein the alkali metal carbonate is $K_2CO_3$ and the support is magnesium oxide.

17. A process for the conversion of terpenes to cymenes which comprises contacting at least one terpene selected from the group comprised of mono- and bicyclic unsaturated hydrocarbons having the formula $C_{10}H_{16}$, with an alkali metal carbonate catalyst on a support, at a temperature of 300° to 475° C., at a liquid hour space velocity (LHSV) of 0.20 to 20.

18. A process according to claim 17 wherein the terpenes are selected from the group consisting of α-pinene, β-pinene, limonene, p-menthane, (cis and trans isomers) terpinolene, terpinene, menthadiene and Δ-3 carene.

19. A process according to claim 17 wherein the alkali metal carbonate is selected from the group consisting of $Na_2CO_3$, $Li_2CO_3$, and $K_2CO_3$.

20. A process according to claim 17 wherein the alkali metal carbonate catalyst is supported on a carrier selected from the group consisting of silica, aluminum oxide, magnesium oxide, carbon and titanium dioxide.

21. A process according to claim 17 wherein the temperature is from 350° to 450° C.

22. A process according to claim 17 wherein the temperature is from 380° to 425° C.

23. A process according to claim 17 wherein the alkali metal carbonate is sodium carbonate and the support is titanium dioxide.

24. A process according to claim 17 wherein the alkali metal carbonate is $K_2CO_3$ and the support is magnesium oxide.

25. A process according to claim 17 wherein the LHSV is from 0.25 to 15.

26. A process according to claim 17 wherein the LHSV is from 0.3 to 10.

27. A process according to claim 17 wherein the LHSV is from 0.4 to 10.

28. A process for the conversion of terpenes to cymenes which comprises contacting at least one terpene selected from the group comprised of mono- and bicyclic unsaturated hydrocarbons having the formula $C_{10}H_{16}$, with $Na_2CO_3$ on an aluminum oxide carrier at a temperature of 400° to 450° C. at a LHSV of 0.4 to 10.

29. A process for the conversion of terpenes to cymenes which comprises contacting at least one terpene selected from the group comprised of mono- and bicyclic unsaturated hydrocarbons having the formula $C_{10}H_{16}$ with $K_2CO_3$ on an aluminum oxide carrier at a temperature of 400° to 450° C. at a LHSV of 0.4 to 10.

30. A process for the conversion of terpenes to cymenes which comprises contacting at least one terpene selected from the group comprised of mono- and bicyclic unsaturated hydrocarbons having the formula $C_{10}H_{16}$, with $Na_2CO_3$ on a magnesium oxide carrier at a temperature of 400° to 450° C. at a LHSV of 0.4 to 10.

* * * * *